US00PP29902P3

(12) United States Plant Patent
Klemm et al.

(10) Patent No.: US PP29,902 P3
(45) Date of Patent: Nov. 27, 2018

(54) POINSETTIA PLANT NAMED 'NPCW16226'

(50) Latin Name: *Euphorbia pulcherrima*
Varietal Denomination: NPCW16226

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 20 days.

(21) Appl. No.: 15/530,397

(22) Filed: Jan. 9, 2017

(65) Prior Publication Data
US 2018/0199484 P1 Jul. 12, 2018

(51) Int. Cl.
*A01H 5/02* (2018.01)

(52) U.S. Cl.
USPC ..... Plt./306
CPC ..... *A01H 5/02* (2013.01)

(58) Field of Classification Search
USPC ..... Plt./306
See application file for complete search history.

*Primary Examiner* — Keith O. Robinson
(74) *Attorney, Agent, or Firm* — Bethany Reid Roahrig; Barbara Campbell; Cochran Freund & Young LLC

(57) ABSTRACT

A new poinsettia plant particularly distinguished by having dark pink bracts and good keeping quality is disclosed.

1 Drawing Sheet

Genus and species: *Euphorbia pulcherrima.*
Variety denomination: 'NPCW16226'.

BACKGROUND OF THE NEW PLANT

The present invention comprises a new and distinct variety of poinsettia, botanically known as *Euphorbia pulcherrima* and hereinafter referred to by the variety name 'NPCW16226'. 'NPCW16226' was derived from an X-ray induced mutation of a proprietary and unpatented red variety known as 'NPCW13208'.

In November 2010, a single plant was selected in Stuttgart, Germany. In April 2011, 'NPCW16226' was first asexually propagated by vegetative apical cuttings. 'NPCW16226' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Dark pink bracts; and
2. Good keeping quality.

DESCRIPTION OF THE PHOTOGRAPH

This new poinsettia plant is illustrated by the accompanying photograph which shows an overall view of the whole plant. The photograph is of a plant approximately 16 to 18 weeks old grown indoors in Stuttgart, Germany in October 2016. The colors shown are as true as can be reasonably obtained by conventional photographic procedures.

DESCRIPTION OF THE NEW VARIETY

The following detailed descriptions set forth the distinctive characteristics of 'NPCW16226'. The data which define these characteristics were collected from asexual reproductions carried out in Stuttgart, Germany. Data was collected on plants 19-weeks-old after potting grown in a greenhouse in Stuttgart, Germany under greenhouse conditions in December 2016. Color references are to The R.H.S. Colour Chart of The Royal Horticultural Society of London (R.H.S.), 5$^{th}$ edition (2007).

Classification:
- *Family.*—Euphorbiaceae.
- *Species.*—*Euphorbia pulcherrima.*
- *Common name.*—Poinsettia.
- *Variety.*—'NPCW16226'.

Parentage: X-ray induced mutation of proprietary unpatented variety 'NPCW13208'.

Growth:
- *Blooming habit.*—Intermittent.
- *Flowering response time.*—Approximately 55 days.
- *Keeping quality.*—Good.

Plant description:
- *Form.*—Triangular.
- *Growth habit.*—Upright.
- *Height.*—32.0 cm to 35.0 cm.
- *Width.*—23.0 cm to 28.0 cm.
- *Average number of inflorescences per plant.*—5 to 6.

Propagation:
- *Type cuttings.*—Apical cuttings.
- *Time to produce a rooted cutting.*—4 weeks.
- *Rooting habit and root color.*—Freely branching and white RHS 155D.

Lateral branches:
- *Color.*—RHS 144A.
- *Length.*—28.0 cm to 31.0 cm.
- *Internode length.*—1.8 cm to 4.0 cm.
- *Diameter.*—0.5 cm to 0.8 cm.
- *Branching habit.*—Freely branching.
- *Number of lateral branches per plant.*—5 to 6.
- *Texture.*—Smooth.

Leaves:

*Quantity.*—6 to 8 per lateral branch.

*Arrangement.*—Alternate.

*Number of lobes on the leaf blade.*—Absent.

*Shape.*—Ovate.

*Apex.*—Acute.

*Base.*—Obtuse.

*Margin.*—Entire.

*Length.*—7.0 cm to 14.0 cm.

*Width.*—6.0 cm to 9.0 cm.

*Texture (both surfaces).*—Smooth.

*Vein color.*—Upper surface: Transparent. Lower surface: RHS 139D.

*Variegation.*—Absent.

*Color.*—Mature foliage: Upper surface: RHS 139A. Lower surface: RHS 139D. Immature foliage: Upper surface: RHS 141A. Lower surface: RHS 139B.

*Leaf petiole.*—Length: 3.5 cm to 6.0 cm. Diameter: 0.2 cm to 0.3 cm. Color: Upper (part) surface: RHS 139D to RHS 59B. Lower (part) surface: RHS 139D. Texture: Smooth. Strength: Medium.

Inflorescence:

*Lastingness of inflorescence on the plant.*—4 weeks.

*Natural flowering season.*—End of November.

*Diameter.*—18.0 cm to 22.0 cm.

*Height.*—3.0 cm to 4.0 cm.

*Fragrance.*—Absent.

Bracts:

*Number of bracts per inflorescence.*—6 to 9.

*Shape.*—Ovate.

*Apex.*—Acute.

*Base.*—Obtuse.

*Margin.*—Mostly entire, older bracts slightly serrate.

*Size.*—Length: 9.0 cm to 12.0 cm. Width: 4.0 cm to 7.0 cm.

*Texture (both upper and lower surfaces).*—Smooth.

*Venation pattern.*—Reticulate.

*Vein color.*—Upper surface: RHS 59B. Lower surface: RHS 181B.

*Bract color.*—Upper surface: Close to RHS 52B. Lower surface: RHS 51D.

*Bract petiole.*—Length: 0.5 cm to 2.5 cm. Diameter: 0.2 cm to 0.3 cm. Color: Upper (part) surface: RHS 59A. Lower (part) surface: RHS 181B. Texture: Smooth. Strength: Medium.

Cyme:

*Diameter.*—1.0 cm to 2.0 cm.

*Cyathia number.*—7 to 10 per inflorescence.

*Deformation of glands of the cyathium.*—Absent.

*Timing of opening of cyathia.*—End of November. First pollen appears in parallel to opening of the nectar cups; stigmas appear 1 to 2 weeks later.

*Cyathium.*—Shape: Ovate. Diameter: 0.2 cm to 0.5 cm. Length: 0.3 cm to 0.8 cm. Color: RHS 143C.

*Peduncle.*—Color: RHS 142B. Length: 0.2 cm to 0.3 cm. Diameter: 0.1 cm. Texture: Smooth. Strength: Medium.

*Nectar cups.*—Number: 1 per cyathium. Diameter: 0.1 cm. Size: 0.4 cm to 0.5 cm. Color: RHS 1C.

Reproductive organs:

*Stamen quantity.*—5 to 10 per cyathium.

*Stamen shape.*—Ovate.

*Filament length.*—0.25 cm.

*Filament color.*—RHS 46A.

*Pollen quantity.*—Moderate.

*Pollen color.*—RHS 12A.

*Gynoecium.*—Present. Pistil quantity per cyanthium: 1. Pistil length: 0.2 cm. Stigma form: Divided in two parts. Stigma color: RHS 183A. Style length: 0.2 cm. Style color: RHS 183A. Ovary length: 0.05 cm. Ovary color: RHS 143C.

Fruit and seed set: Not observed.

Disease and pest resistance: No special disease or pest resistance observed.

COMPARISON WITH PARENTAL AND KNOWN VARIETY

'NPCW16226' is a distinct variety of poinsettia having dark pink bracts. 'NPCW16226' is distinguished from parental line 'NPCW13208' as described in Table 1.

TABLE 1

| Characteristic | Variety 'NPCW16226' | 'NPCW13208' |
|---|---|---|
| Bract color | Dark pink (close to RHS 52B) | Red |

'NPCW16226' is distinguished from commercial line 'Christmas Feelings Pink' (U.S. Plant Pat. No. 20,222) also known as 'NPCW07120' as described in Table 2.

TABLE 2

| Characteristic | Variety 'NPCW16226' | 'Christmas Feelings Pink' |
|---|---|---|
| Bract color | Close to RHS 52B | Darker than RHS 58B/C |
| Vigor | Compact - medium | Very strong |

We claim:

1. A new and distinct variety of poinsettia plant named 'NPCW16226' as illustrated and described herein.

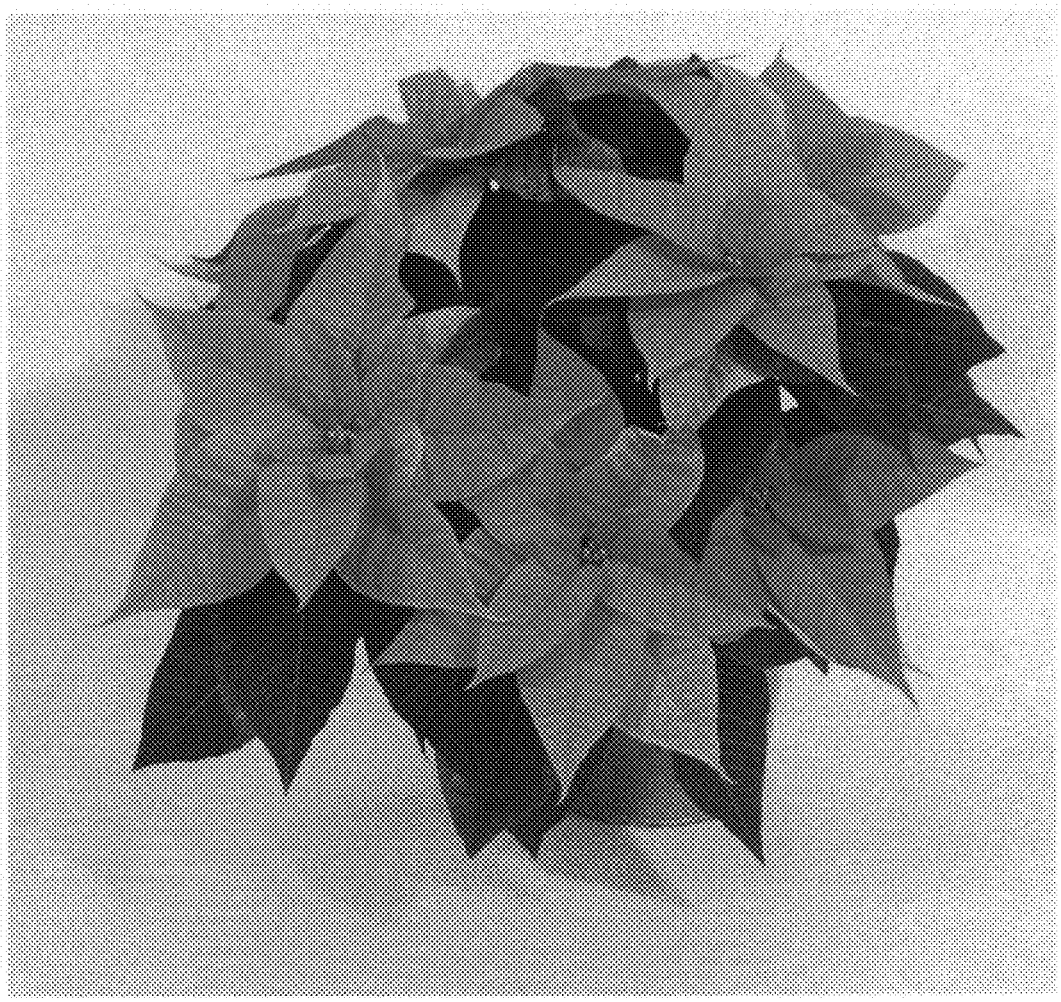

* * * * *